United States Patent
Chakraborty et al.

(10) Patent No.: US 10,856,881 B2
(45) Date of Patent: Dec. 8, 2020

(54) LEFT ATRIAL APPENDAGE OCCLUSION DEVICE DELIVERY SYSTEM

(71) Applicant: Flow MedTech, Inc., Kingsport, TN (US)

(72) Inventors: Arnab Ranjan Chakraborty, Johnson City, TN (US); Christine Tu-Anh Hang, Aiken, SC (US)

(73) Assignee: FLOW MEDTECH, INC., Kingsport, TN (US)

( * ) Notice: Subject to any disclaimer, the term of this patent is extended or adjusted under 35 U.S.C. 154(b) by 271 days.

(21) Appl. No.: 15/512,675

(22) PCT Filed: Sep. 18, 2015

(86) PCT No.: PCT/US2015/050967
§ 371 (c)(1),
(2) Date: Mar. 20, 2017

(87) PCT Pub. No.: WO2016/044740
PCT Pub. Date: Mar. 24, 2016

(65) Prior Publication Data
US 2017/0290594 A1 Oct. 12, 2017

Related U.S. Application Data

(60) Provisional application No. 62/052,480, filed on Sep. 19, 2014.

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 17/12136* (2013.01);
(Continued)

(58) Field of Classification Search
CPC .......... A61B 17/0057; A61B 17/00632; A61B 17/12022; A61B 17/12122;
(Continued)

(56) References Cited

U.S. PATENT DOCUMENTS 4,545,367 A * 10/1985 Tucci ............... A61B 17/12109
128/898
4,836,204 A 6/1989 Landymore et al.
(Continued)

FOREIGN PATENT DOCUMENTS

| WO | 2007130724 A2 | 11/2007 |
|----|---------------|---------|
| WO | 2013068466 A1 | 5/2013 |
| WO | 2013192332 A2 | 12/2013 |

OTHER PUBLICATIONS

International Search Report and Written Opinion dated Dec. 17, 2015 in related International Patent Application PCT/US2015/050967.
(Continued)

*Primary Examiner* — Todd J Scherbel
(74) *Attorney, Agent, or Firm* — Morris, Manning & Martin, LLP; Bryan D. Stewart

(57) ABSTRACT

In various embodiments, a system for delivering an implantable device inside a body cavity includes: 1) a core cannula; 2) an access sheath; 3) an injection apparatus for filling the implantable device with one or more fluids; and 4) expanding members operatively connected to the core cannula for preventing the core cannula from advancing through a body orifice once the core cannula and expanding members exist the access sheath. According to particular embodiments, a distal end of the core cannula is pre-attached to the implantable device through a device locking member. In one or more embodiments, upon assessment, an injection apparatus is removed using an injection apparatus handle, the implant-
(Continued)

able device is detached from the core cannula via a device deployment handle (to be implanted), and the access sheath is removed.

20 Claims, 14 Drawing Sheets

(52) U.S. Cl.
CPC .. *A61B 17/12145* (2013.01); *A61B 2017/003* (2013.01); *A61B 2017/00022* (2013.01); *A61B 2017/0096* (2013.01); *A61B 2017/00867* (2013.01); *A61B 2017/00876* (2013.01); *A61B 2017/1205* (2013.01); *A61B 2017/12054* (2013.01); *A61B 2017/12081* (2013.01); *A61B 2017/12086* (2013.01); *A61B 2017/12095* (2013.01)

(58) Field of Classification Search
CPC .... A61B 17/12136; A61B 2017/00243; A61B 2017/00575; A61B 2017/1205; A61B 2017/12054; A61B 2017/12081; A61B 2017/12086; A61B 2017/12095; A61M 2025/1054

See application file for complete search history.

(56) References Cited

U.S. PATENT DOCUMENTS

| | | | |
|---|---|---|---|
| 4,917,089 A | 4/1990 | Sideris | |
| 5,433,727 A | 7/1995 | Sideris | |
| 5,634,936 A | 6/1997 | Linden et al. | |
| 5,792,179 A | 8/1998 | Sideris | |
| 6,019,778 A | 1/2000 | Wilson et al. | |
| 6,123,715 A | 9/2000 | Amplatz | |
| 6,152,144 A | 11/2000 | Lesh et al. | |
| 6,238,416 B1 | 5/2001 | Sideris | |
| 6,293,960 B1 | 9/2001 | Ken | |
| 6,368,339 B1 | 4/2002 | Amplatz | |
| 6,375,668 B1 | 4/2002 | Gifford et al. | |
| 6,447,531 B1 | 9/2002 | Amplatz | |
| 6,579,303 B2 | 6/2003 | Amplatz | |
| 6,652,556 B1 | 11/2003 | VanTassel et al. | |
| 6,730,108 B2 | 5/2004 | Van Tassel et al. | |
| 6,949,113 B2 | 9/2005 | Van Tassel et al. | |
| 6,981,980 B2 | 1/2006 | Sampson et al. | |
| 6,994,092 B2 | 2/2006 | Van Der Burg et al. | |
| 7,128,073 B1 | 10/2006 | Van Der Burg et al. | |
| 7,152,605 B2 | 12/2006 | Khairkhahan et al. | |
| 7,284,488 B2 | 10/2007 | Maruyama et al. | |
| 7,318,829 B2 | 1/2008 | Kaplan et al. | |
| 7,537,012 B2 | 5/2009 | Mohanraj | |
| 7,566,336 B2 | 7/2009 | Corcoran et al. | |
| 7,597,704 B2 | 10/2009 | Frazier et al. | |
| 7,665,466 B2 | 2/2010 | Figulla et al. | |
| 7,842,069 B2 | 11/2010 | Widomski et al. | |
| 7,955,354 B2 | 6/2011 | Figulla et al. | |
| 8,080,032 B2 | 12/2011 | Van Der Burg et al. | |
| 8,097,015 B2 | 1/2012 | Devellian | |
| 8,100,938 B2 | 1/2012 | Figulla et al. | |
| 8,152,758 B2 | 4/2012 | Chan et al. | |
| 8,221,445 B2 | 7/2012 | Van Tassel et al. | |
| 8,523,897 B2 | 9/2013 | Van Der Burg et al. | |
| 8,535,343 B2 | 9/2013 | Van Der Burg et al. | |
| 8,545,530 B2 | 10/2013 | Eskridge et al. | |
| 8,562,643 B2 | 10/2013 | Tekulve et al. | |
| 8,597,324 B2 | 12/2013 | Briganti et al. | |
| 8,636,732 B2 | 1/2014 | Davis et al. | |
| 8,636,764 B2 | 1/2014 | Miles et al. | |
| 8,647,361 B2 | 2/2014 | Borillo et al. | |
| 8,663,245 B2 | 3/2014 | Francischelli et al. | |
| 8,663,268 B2 | 3/2014 | Quinn et al. | |
| 8,663,273 B2 | 3/2014 | Khairkhahan et al. | |
| 8,685,055 B2 | 4/2014 | Van Tassel et al. | |
| 8,690,910 B2 | 4/2014 | Carley et al. | |
| 8,690,911 B2 | 4/2014 | Miles et al. | |
| 8,715,302 B2 | 5/2014 | Ibrahim et al. | |
| 8,715,318 B2 | 5/2014 | Miles et al. | |
| 8,721,663 B2 | 5/2014 | Kaplan et al. | |
| 8,740,934 B2 | 6/2014 | McGuckin, Jr. | |
| 8,747,452 B2 | 6/2014 | Fischell et al. | |
| 8,747,454 B2 | 6/2014 | Khairkhahan et al. | |
| 8,753,303 B2 | 6/2014 | Weisman et al. | |
| 8,764,765 B2 | 7/2014 | Piskun et al. | |
| 8,764,793 B2 | 7/2014 | Lee | |
| 8,814,931 B2 | 8/2014 | Wang et al. | |
| 9,770,234 B2 | 9/2017 | Sideris et al. | |
| 10,076,335 B2 | 9/2018 | Zaver et al. | |
| 2003/0114913 A1 | 6/2003 | Spenser et al. | |
| 2003/0149463 A1 | 8/2003 | Solymar et al. | |
| 2004/0254594 A1 | 12/2004 | Alfaro | |
| 2005/0004652 A1* | 1/2005 | van der Burg | A61B 17/0057 623/1.12 |
| 2005/0033331 A1 | 2/2005 | Burnett et al. | |
| 2005/0070957 A1 | 3/2005 | Das | |
| 2005/0113861 A1 | 5/2005 | Corcoran et al. | |
| 2005/0177182 A1 | 8/2005 | Van Der Burg et al. | |
| 2005/0216052 A1 | 9/2005 | Mazzocchi et al. | |
| 2005/0234543 A1 | 10/2005 | Glaser et al. | |
| 2006/0020278 A1 | 1/2006 | Burnett et al. | |
| 2006/0020327 A1 | 1/2006 | Lashinski | |
| 2006/0265043 A1 | 11/2006 | Mandrusov et al. | |
| 2007/0083224 A1 | 4/2007 | Hively | |
| 2007/0083230 A1 | 4/2007 | Javois | |
| 2007/0129753 A1 | 6/2007 | Quinn et al. | |
| 2007/0135826 A1 | 6/2007 | Zaver et al. | |
| 2007/0179345 A1 | 8/2007 | Santilli | |
| 2008/0033457 A1 | 2/2008 | Francischelli et al. | |
| 2008/0215031 A1* | 9/2008 | Belfort | A61B 17/12099 604/500 |
| 2009/0099596 A1 | 4/2009 | McGuckin, Jr. et al. | |
| 2009/0149879 A1 | 6/2009 | Dillon | |
| 2009/0171428 A1 | 7/2009 | Hansen | |
| 2009/0209999 A1 | 8/2009 | Afremov | |
| 2010/0185233 A1 | 7/2010 | Thommen | |
| 2011/0022079 A1 | 1/2011 | Miles et al. | |
| 2011/0077622 A1* | 3/2011 | Weisman | A61F 2/95 604/544 |
| 2011/0178539 A1 | 7/2011 | Holmes, Jr. et al. | |
| 2011/0288558 A1 | 11/2011 | Nimgaard | |
| 2012/0116269 A1 | 5/2012 | McAuley | |
| 2012/0191125 A1 | 7/2012 | Babkes et al. | |
| 2012/0271343 A1 | 10/2012 | Borillo et al. | |
| 2012/0283585 A1 | 11/2012 | Werneth et al. | |
| 2012/0283773 A1 | 11/2012 | Van Tassel et al. | |
| 2012/0289776 A1 | 11/2012 | Keast et al. | |
| 2013/0018413 A1 | 1/2013 | Oral et al. | |
| 2013/0116724 A1 | 5/2013 | Clark et al. | |
| 2013/0138138 A1 | 5/2013 | Clark et al. | |
| 2013/0190799 A1 | 7/2013 | Clark | |
| 2013/0218192 A1 | 8/2013 | Erzberger et al. | |
| 2013/0218193 A1 | 8/2013 | Erzberger et al. | |
| 2013/0237908 A1 | 9/2013 | Clark | |
| 2013/0331884 A1 | 12/2013 | Van Der Burg et al. | |
| 2013/0338696 A1 | 12/2013 | Sideris | |
| 2014/0039536 A1 | 2/2014 | Cully et al. | |
| 2014/0058371 A1 | 2/2014 | Krishnan | |
| 2014/0074151 A1 | 3/2014 | Tischler et al. | |
| 2014/0100596 A1 | 4/2014 | Rudman et al. | |
| 2014/0107696 A1 | 4/2014 | Borillo et al. | |
| 2014/0114340 A1 | 4/2014 | Zhou et al. | |
| 2014/0163605 A1 | 6/2014 | Van Tassel et al. | |
| 2014/0188157 A1 | 7/2014 | Clark | |
| 2015/0151826 A1 | 6/2015 | Geneste | |
| 2016/0100843 A1 | 4/2016 | Sideris | |
| 2016/0192912 A1 | 7/2016 | Kassab et al. | |
| 2017/0143318 A1 | 5/2017 | Hu | |
| 2018/0338767 A1 | 11/2018 | Dasnurkar et al. | |
| 2018/0360432 A1 | 12/2018 | Corcoran et al. | |
| 2018/0368820 A1 | 12/2018 | Rad et al. | |
| 2018/0368855 A1 | 12/2018 | Edmiston et al. | |
| 2018/0368856 A1 | 12/2018 | Miles et al. | |

(56) References Cited

U.S. PATENT DOCUMENTS

| | | |
|---|---|---|
| 2018/0369594 A1 | 12/2018 | Werneth et al. |
| 2019/0000604 A1 | 1/2019 | Eli |
| 2019/0008495 A1 | 1/2019 | Li |
| 2019/0008626 A1 | 1/2019 | Janardhan et al. |
| 2019/0009057 A1 | 1/2019 | Li et al. |
| 2019/0015109 A1 | 1/2019 | Li |
| 2019/0021711 A1 | 1/2019 | Li |
| 2019/0021741 A1 | 1/2019 | Chen et al. |
| 2019/0038294 A1 | 2/2019 | Tieu et al. |
| 2019/0038316 A1 | 2/2019 | Gillespie et al. |
| 2019/0046170 A1 | 2/2019 | Coyle et al. |
| 2019/0046210 A1 | 2/2019 | Bowman |
| 2019/0046213 A1 | 2/2019 | Gong et al. |
| 2019/0053810 A1 | 2/2019 | Griffin |
| 2019/0069901 A1 | 3/2019 | Forbes |
| 2019/0071800 A1 | 3/2019 | Koppe |
| 2019/0076136 A1 | 3/2019 | Zhang et al. |
| 2019/0083075 A1 | 3/2019 | Onushko et al. |
| 2019/0088368 A1 | 3/2019 | Grodzki et al. |
| 2019/0090841 A1 | 3/2019 | Degertekin et al. |
| 2019/0090884 A1 | 3/2019 | Bowman |
| 2019/0090885 A1 | 3/2019 | Zhou et al. |
| 2019/0090945 A1 | 3/2019 | Whayne et al. |
| 2019/0090951 A1 | 3/2019 | Camus et al. |
| 2019/0099062 A1 | 4/2019 | Ishihara et al. |
| 2019/0110796 A1 | 4/2019 | Jayaraman |
| 2019/0110880 A1 | 4/2019 | Fox et al. |
| 2019/0117204 A1 | 4/2019 | Wang et al. |
| 2019/0117229 A1 | 4/2019 | Ibrahim et al. |
| 2019/0117260 A1 | 4/2019 | Ahmad |
| 2019/0117300 A1 | 4/2019 | Whayne et al. |
| 2019/0125302 A1 | 5/2019 | Clark |
| 2019/0125350 A1 | 5/2019 | Fung et al. |
| 2019/0125362 A1 | 5/2019 | Tischler |
| 2019/0125375 A1 | 5/2019 | Palushi et al. |
| 2019/0125400 A1 | 5/2019 | Ibrahim et al. |
| 2019/0125439 A1 | 5/2019 | Rohl et al. |
| 2019/0125513 A1 | 5/2019 | Purcell et al. |
| 2019/0125938 A1 | 5/2019 | Chen et al. |
| 2019/0133528 A1 | 5/2019 | Kassab et al. |
| 2019/0133563 A1 | 5/2019 | Glimsdale |
| 2019/0133744 A1 | 5/2019 | Janardhan et al. |
| 2019/0133745 A1 | 5/2019 | Janardhan et al. |
| 2019/0133746 A1 | 5/2019 | Janardhan et al. |
| 2019/0142300 A1 | 5/2019 | Friedman et al. |
| 2019/0142428 A1 | 5/2019 | Widenhouse et al. |
| 2019/0142431 A1 | 5/2019 | Liu et al. |
| 2019/0142434 A1 | 5/2019 | Miller |
| 2019/0142567 A1 | 5/2019 | Janardhan et al. |
| 2019/0142568 A1 | 5/2019 | Janardhan et al. |
| 2019/0150932 A1 | 5/2019 | Cruise et al. |
| 2019/0150937 A1 | 5/2019 | Kassab |

OTHER PUBLICATIONS

European Search Report and Written Opinion dated Nov. 16, 2017 for European Patent Application No. 15783150.4.
European Search Report and Written Opinion dated Sep. 3, 2018 for European Patent Application No. 15842602.3.
International Search Report and Written Opinion dated Jul. 28, 2015 for related International Patent Application PCT/US2015/027666.
"Transcatheter Patch." Custom Medical Devices. Custom Medical Devices, n.d. Web. Jul. 29, 2014. http://www.custommedicaldevices.net/products/transcatheter-patch/.

* cited by examiner

LEFT ATRIAL APPENDAGE OCCLUSION DEVICE DELIVERY SYSTEM

CROSS-REFERENCE TO RELATED APPLICATIONS

This application is a national stage application of and claims the benefit of and priority under 35 U.S.C. § 371 to International Patent Application No. PCT/US2015/050967, filed Sep. 18, 2015, entitled "LEFT ATRIAL APPENDAGE OCCLUSION DEVICE DELIVERY SYSTEM," and under 35 U.S.C. §§ 119, 120 to U.S. Provisional Patent No. 62/052,480, filed Sep. 19, 2014, entitled "LEFT ATRIAL APPENDAGE OCCLUSION DEVICE DELIVERY SYSTEM," each of which are incorporated herein by reference in their entireties.

TECHNICAL FIELD

The present disclosure relates generally to medical devices and delivery systems for the same.

BACKGROUND

The left atrial appendage (LAA) originates from the left wall of the left atrium. This fingerlike projection opens to the atrium through an ovoid orifice and extends 2-4 cm long, pointing towards the apex.

Atrial fibrillation (AF) is the most common arrhythmia (i.e. irregularly timed contraction) and oftentimes occurs due to sustained increased left atrial afterload—leading to an enlargement of the left atrium (LA). The presence of AF may establish a positive feedback loop that furthers enlargement and increases the probability of thrombus (i.e. clotting) formation. As the LAA is not contracting on time, blood stasis occurs in the appendage as the blood flows into the appendage but does not flow out in a rhythmic fashion. This leads to blood clotting in the appendage, which then becomes a risk as the irregular contraction of the LAA may force the clot to travel out of the appendage and into the brain, leading to an ischemic stroke.

It is believed by researchers that up to 90 percent of the clots found in the brain come from the LAA. If AF patients are not treated, their risk of stroke increases as they age; 15 percent of all strokes are caused by AF. However, in patients 70 years and older, more than 20 to 25 percent of strokes are caused by atrial fibrillation.

Current research suggests that occlusion of the left atrial appendage reduces the risk of ischemic stroke in atrial fibrillation patients by preventing LAA thrombus formation from occurring. It also acts as an alternative therapy to oral anticoagulation (OAC). Some patients elect to not take OACs or are ineligible due to side effects.

Delivering a left atrial appendage occlusion device may be challenging due to varying LAA morphologies. Thus, flush deployment of an LAA occlusion device may not easily be achieved. It is in an objective of this invention to provide a flush deployment of a LAA occlusion device through an improved delivery system.

BRIEF SUMMARY OF THE DISCLOSURE

According to various embodiments, the systems and methods herein include an apparatus for delivering a medical device to one or more bodily orifices, the apparatus including: A) a substantially cylindrical core cannula having a proximal end and a distal end; B) a locking member operatively coupled to the distal end of the core cannula; C) one or more expandable members coupled to the distal end of the core cannula, wherein the one or more expandable members are configured for expanding from a compressed position to an expanded position; and D) one or more injection apparatuses inserted into a hollow portion along a length of the core cannula, the one or more injection apparatuses defining at least one opening at a distal end for transmitting fluid.

In one or more embodiments, the systems and methods herein include a medical device delivery system, the delivery system including: A) a substantially cylindrical core cannula having a proximal end and a distal end; B) a locking member operatively coupled to the distal end of the core cannula; C) one or more expandable members coupled to the distal end of the core cannula, wherein the one or more expandable members: i) have a substantially circular cross-section; ii) are compressible from an expanded position to a compressed position; and iii) remain compressed within a hollow access sheath; D) a substantially cylindrical injection apparatus inserted into a hollow portion along a length of the core cannula, the injection apparatus defining at least one opening at a distal end for transmitting fluid; and E) the hollow access sheath, wherein the hollow access sheath surrounds a portion of the length of the core cannula, the locking member, and the one or more expandable members.

In at least one embodiment, the systems and methods herein include a method for delivering an implantable medical device, the method including: A) providing a delivery system detachably connected to an implantable medical device, the delivery system including: i) a substantially cylindrical core cannula having a proximal end and a distal end; ii) a locking member operatively coupled to the distal end of the core cannula; iii) one or more expandable members coupled to the distal end of the core cannula, wherein the one or more expandable members are configured for expanding from a compressed position to an expanded position; and iv) at least one injection apparatus inserted into a hollow portion along a length of the core cannula, the at least one injection apparatus defining at least one opening at a distal end for transmitting fluid; B) threading the delivery system through a hollow access sheath through a patient to an area of implant; C) causing the one or more expandable members to exit the hollow access sheath and thereby expanding to the expanded position; D) injecting fluid into the implantable medical device via the at least one injection apparatus thereby causing the implantable medical device to expand; and E) detaching the implantable medical device from the delivery system.

BRIEF DESCRIPTION OF THE DRAWINGS

Further features and benefits of the present disclosure will be apparent from a detailed description of various embodiments thereof taken in conjunction with the following drawings, wherein similar elements are referred to with similar reference numbers, and wherein.

DETAILED DESCRIPTION

Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

For the purpose of promoting an understanding of the principles of the present disclosure, reference will now be made to the embodiments illustrated in the figures and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

This application is related to and incorporates by reference herein the following U.S. and international patent applications:

U.S. Provisional Patent Appln. No. 61/984,342, entitled "LEFT ATRIAL APPENDAGE OCCLUSION DEVICE", filed on Apr. 25, 2014; and PCT Appln. No. PCT/US15/27666, entitled "LEFT ATRIAL APPENDAGE OCCLUSION DEVICE", filed on Apr. 24, 2015.

The above references are incorporated by reference herein. Any incorporation by reference is not intended to give a definitive or limiting meaning of a particular term. In the case of a conflict of terms, this document governs.

Overview

The present systems and methods relate to a system of delivering an implantable, inflatable device comprising of soft polymeric material(s) with a one-way sealing system and insertable fluid for inflation while keeping the device flush to the surrounding tissue. In various embodiments, the present systems and methods relate to a system of delivering an implantable, inflatable device for occupying body cavities, e.g. the left atrial appendage, etc.

Exemplary delivery devices such as those disclosed herein may provide several advantages over previous delivery systems, including giving a user of the exemplary delivery device an ability to deploy an implant device inside a body cavity flush with nearby tissue walls by one or more expandable members attached to the delivery system, deployed through, in some embodiments, a standard transseptal procedure providing a secure and slender attachment to an implant device.

Exemplary Device Structure

Figure 1:
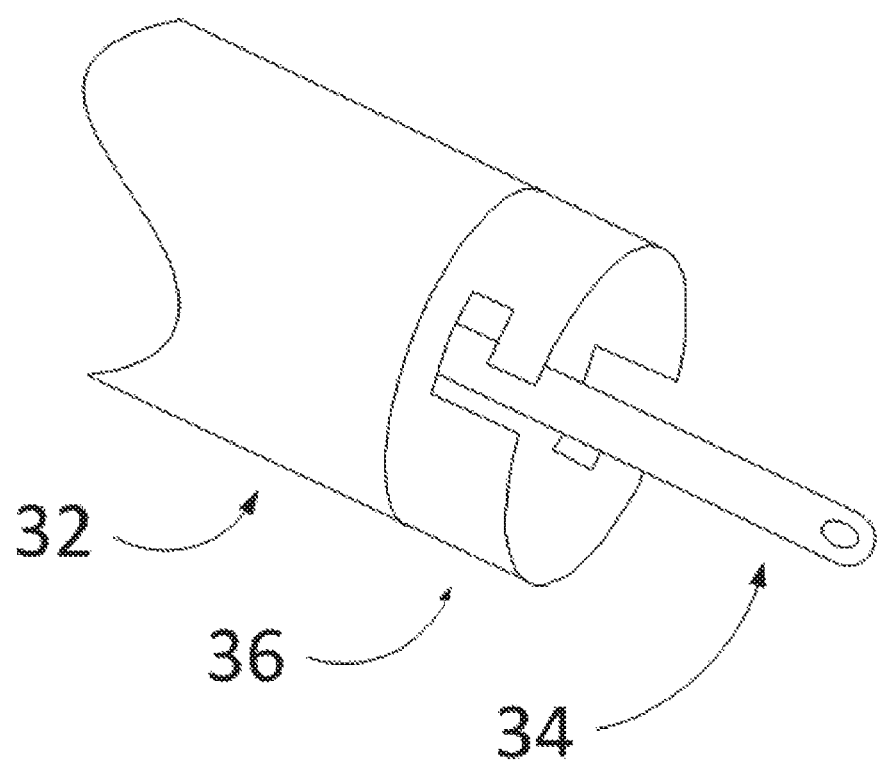
FIG. 1 shows an exemplary delivery device, according to one embodiment of the present disclosure.

Turning now to the figures, in the embodiment shown in FIG. 1, an exemplary delivery system includes: 1) a core cannula 32, 2) a device locking member 36 operatively connected to a distal end of the core cannula 32, and 3) an injection apparatus 34 extending through the core cannula 32. As will be understood by one of ordinary skill in the art (and as further discussed herein), the exemplary delivery system is attached to an exemplary occlusion device (or another device) and threaded through a access sheath into a patient for deployment of the exemplary occlusion device.

In various embodiments, the exemplary core cannula 32 is constructed from polymeric materials, including polyurethane, latex, Pebax, nylon, PET or silicone. According to particular embodiments, the core cannula 32 is hollow, thin-walled, and contains a central smaller hole at the proximal end for an injection apparatus or multiple injection apparatuses (e.g., injection apparatus 34) to pass through. In particular embodiments, the outer diameter of the core cannula 32 will allow the transport of an implantable device within (e.g., 8 Fr (2.666 mm), 10 Fr (3.333 mm), 12 Fr (4 mm), etc.). In at least one embodiment, the length of the core cannula is enough to reach from an access point on a patient to the delivery destination, such as the patient's LAA (e.g., usable length of 75 cm, 85 cm, 95 cm. etc.).

In one or more embodiments, the hollow injection apparatus 34 allows for fluid to pass through to inflate a device that may be attached to the device locking member 36. The injection apparatus 34 may be formed of metallic materials, shape memory materials, fiber reinforced materials, and/or polymer materials. In various embodiments, there are one or more injection apparatus containing one or more holes or various shapes (e.g., circular, ovular, etc.) and sizes (e.g., 0.25 mm, 0.5 mm, 0.75 mm, etc.) per apparatus along the exterior distal length. In particular embodiments, the distal end of the one or more injection apparatuses are rounded or blunt to reduce the risk of puncturing tissue or a compliant attached device. In at least one embodiment, the outer diameter of the injection apparatus 34 will allow the transport of fluid (e.g. contrast, sterile water, saline, hydrogels, or non-viscous to semi-viscous fluids) to an implantable device (e.g., 1 mm, 1.5 mm, 2 mm, etc.). The length of the injection apparatus is enough to reach from a user end of a delivery system (FIG. 4) to an implantable device at a delivery destination of an implantable device, such as a patient's LAA (e.g., 75 cm, 85 cm, 95 cm, etc.). The injection apparatus or injection apparatuses 34 may be of any suitable cross sectional shape or shapes, including, but not limited to, substantially cylindrical, substantially rectangular, substantially trapezoidal, etc.

In at least one embodiment, the device locking member 36, which may be constructed out of metal materials (e.g., aluminum, nitinol, stainless steel, etc.) or polymeric material(s) (e.g., silicone, polyurethane, etc.), is located at the distal end of the core cannula 32 and allows for attachment/detachment of a connected device (as further discussed herein). The device locking member 36 may be attached to the core cannula 32 through a fastening method (e.g., adhesives, screws, welding, etc.) and/or may be at least partially or fully integrally formed with the core cannula 32. The device locking member 36 may operate as a twist lock method or luer lock method such that the device could untwist from a helical thread or unlock from an indentation within the device locking member 36. In the embodiment shown in FIGS. 1 and 2 and further discussed herein, the device locking member 36 may include one or more substantially L-shaped channels terminating at a distal end of the device locking member 36 to allow for attachment/detachment of an exemplary occlusion device.

Figure 2:
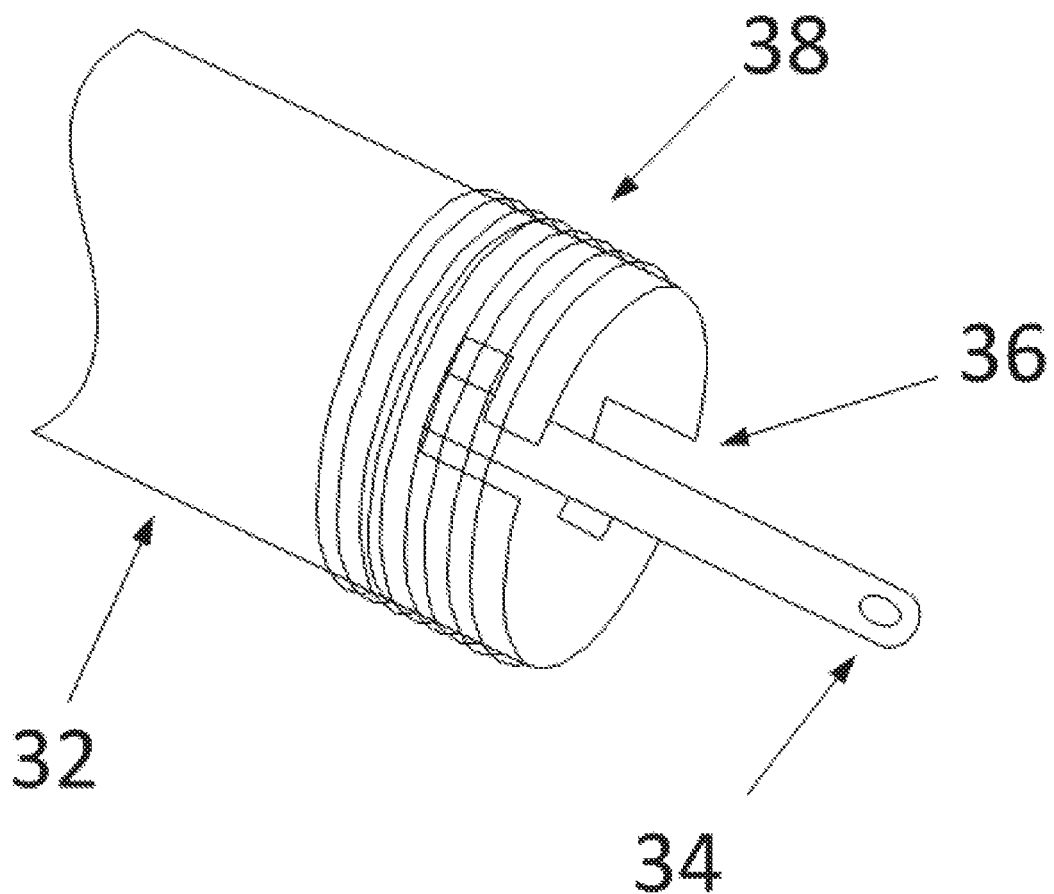
FIG. 2 shows the exemplary delivery device of FIG. 1, without the expanding members, according to one embodiment of the present disclosure.

Turning now to FIG. 2, the embodiment shown depicts the exemplary delivery device of FIG. 1 with exemplary expanding members 38 operatively connected to the core cannula 32 at a distal end. In various embodiments, the expanding members 38 can be attached to the core cannula using methods, such as, but not limited to, adhesives or wiring. In some embodiments, the expanding members 38 include one or more circular wire-like member that may be constructed from Nitinol, stainless steel, cobalt chromium, metal alloy, polymer, ceramic, shape-memory materials, or a combination of these materials.

Figure 3:
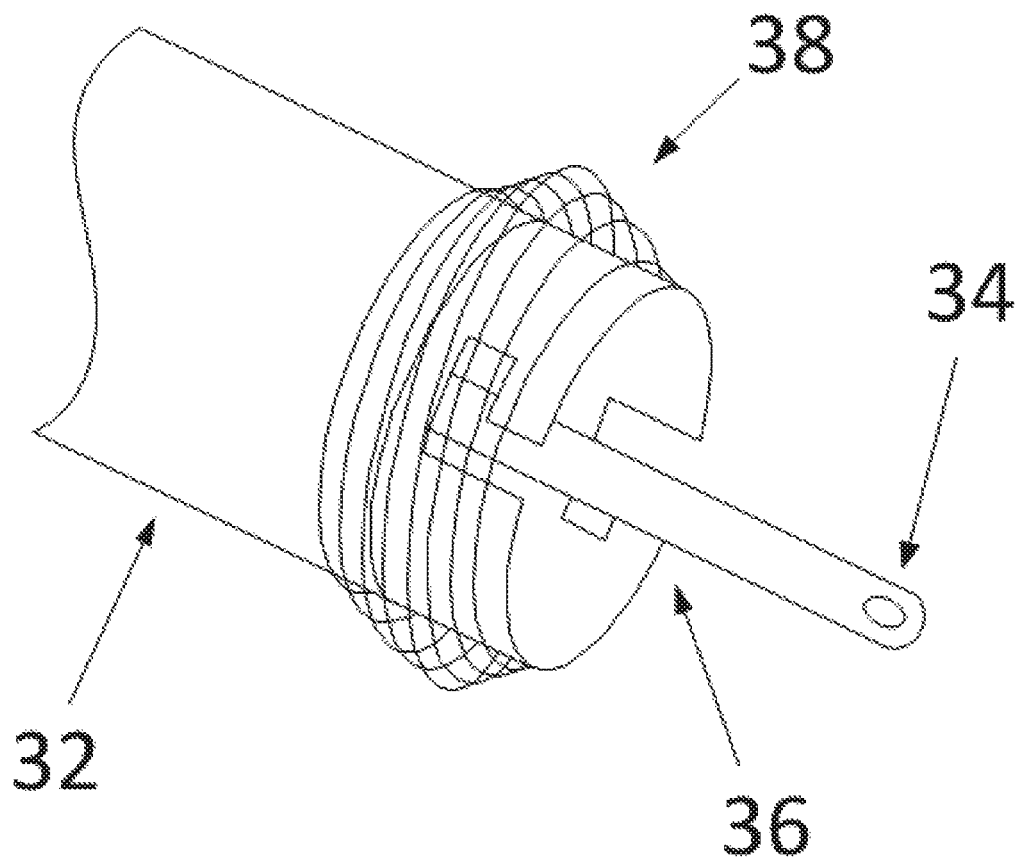
FIG. 3 shows exemplary expanding members attached to the core cannula and fully expanded, according to one embodiment of the present disclosure.

FIG. 3 depicts the exemplary delivery device of FIG. 2, with the expanding members 38 expanded. In the embodiment shown, the expanding members, when expanded, generally form an eggbeater shape. In various embodiments, the expanding members 38 may generally form triangular, ovular, and multiangular shapes. In particular embodiments, an adhering element may be constructed from various metal alloys or adhesives to keep the core cannula expanding members 38 from expanding horizontally The expanding members 38 may be configured to expand under a number of suitable conditions and/or via a number of suitable mechanisms. According to particular embodiments, the expanding members 38 expand once exposed inside the body and will compressed upon being retrieved through an access sheath (e.g., the expanding members are compressed at a first diameter by the diameter of the access sheath and expand upon exiting the access sheath to a predetermined second diameter. In various embodiments, the expanding members 38 expand through a method (e.g., trigger, sensor, feedback system etc.) on the user end of an exemplary delivery system as shown in FIG. 4, extending down the core cannula 32, or remotely.

Figure 4:
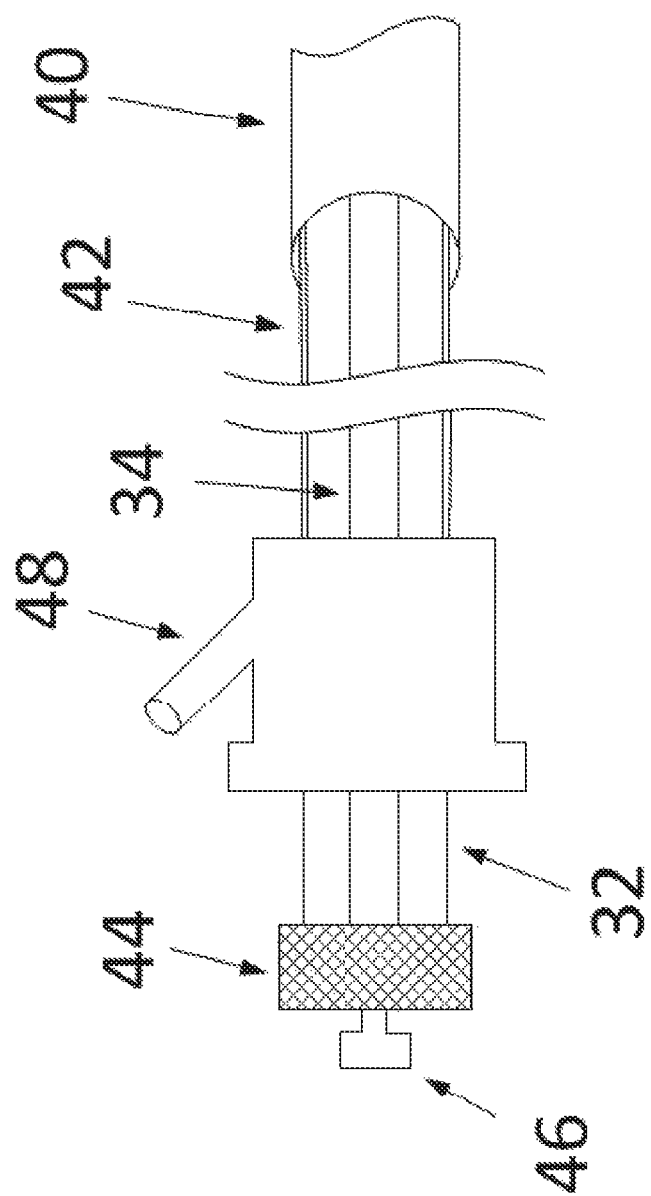
FIG. 4 shows a proximal or user end of an exemplary delivery system, according to one embodiment of the present disclosure.

Turning now to FIG. 4, the embodiment shown depicts a proximal or user end of an exemplary delivery system. The embodiment shown includes 1) an injection apparatus handle 46, 2) a device deployment handle 44, 3) a core cannula 32, 4) a hemostasis valve 48, 5) an injection apparatus 34, 6) a delivery catheter 42, and 7) an access sheath 40. In some embodiments, the hemostasis valve 48 is located at the proximal end of the hollow access sheath 40 to prevent backflow of fluid and air penetration into the system. In various embodiments, the hemostasis valve 48 can be constructed from materials that include but are not limited to polycarbonate, polyethylene, silicone, polyurethane, PVC, EPDM, stainless steel, combinations of polymeric materials, or combinations of metal alloys. The hemostasis valve 48 may be constructed through injection molding, dip molding, or various techniques known to those skilled in the art. In various embodiments, the hemostasis valve 48 may be attached to the access sheath 40 via adhesives, welding, molding techniques, turning, riling operations, drilling operations, or bending operations.

In particular embodiments, the injection apparatus handle 46 is located at the proximal end of an injection apparatus 34 for maneuvering the length of the injection apparatus 34 and any injection fluids that may be passed through the injection apparatus 34. In particular embodiments, the delivery system may include multiple injection apparatuses 34. In these embodiments, there may be one or more injection apparatus handles 46 attached to one or more corresponding injection apparatus 34 through adhesives, welding, and/or molding techniques.

In at least one embodiment, the delivery catheter member 42 travels through the hollow access sheath 40 and is attached to the core cannula 32, the device deployment handle 44, or body of the core cannula 32 through methods such as adhesives, welding, or molding techniques. In particular embodiments, the device deployment handle 44 controls the detachment of an implantable device operatively connected to the distal end of the core cannula 32 (not shown in FIG. 4). In at least one embodiment, the device deployment handle 44 is located at the proximal end of the core cannula 32 and is adhered to the core cannula 32 via an adhesive, by welding, and/or through molding techniques. In some embodiments, the device deployment handle 44 and an injection apparatus handle 46 may be constructed from materials that include but are not limited to Pebax, polyurethane, Nylon, silicone, polycarbonate, polyethylene, PVC, EPDM, stainless steel, combinations of polymeric materials, or combinations of metal alloys. In further embodiments, the device deployment handle 44 and an injection apparatus handle 46 may be integrally formed by molding, casting, 3D printing, or other suitable method.

Figure 5:
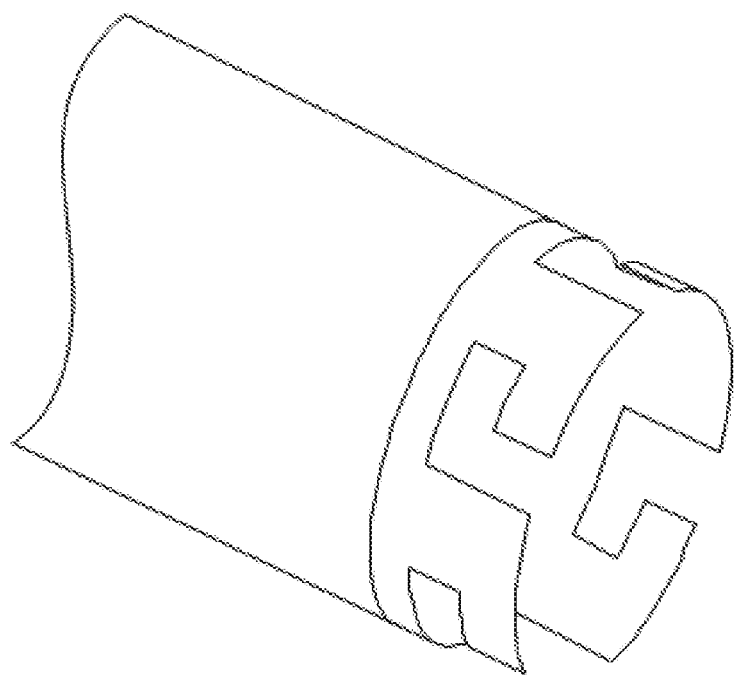
FIG. 5 shows an exemplary delivery device locking system of an exemplary delivery device, according to one embodiment of the present disclosure.
Figure 6:
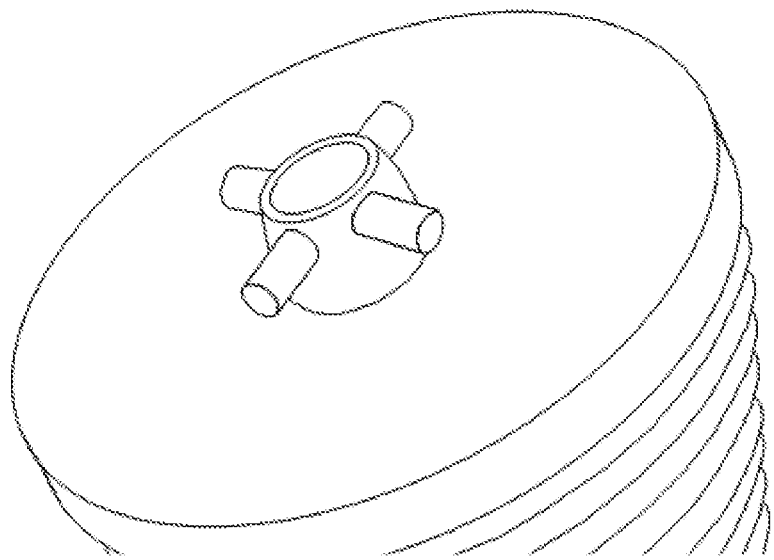
FIG. 6 shows an exemplary occlusion device locking system of an exemplary occlusion device, according to one embodiment of the present disclosure.

FIG. 5 depicts an exemplary device locking member (e.g., device locking member 36). In the embodiment shown, the device locking member 36 is a twist locking mechanism with an "L" shaped channel that allows the attachment and detachment of core cannula 32 to an exemplary implantable device as shown in FIG. 6. The function of an exemplary device locking member 36 is controlled by methods such as a trigger, sensor, switch, etc. on a user (proximal) end of an exemplary delivery system. In various embodiments, the device locking member 36 may be in the form of but not limited to a threaded mechanism (e.g., external, internal), leur lock, magnet, etc. The device locking member 36 is found at the distal end of core cannula 32 and may be attached to the core cannula 32 through a fastening method (e.g., adhesives, screws, welding, etc.) or may be an extension of the core cannula 32.

FIG. 6 depicts an exemplary locking member of an exemplary implantable device as discussed herein. Details of exemplary implantable devices are further discussed in PCT Appln. No. PCT/US15/27666, entitled "LEFT ATRIAL APPENDAGE OCCLUSION DEVICE", filed on Apr. 24, 2015, incorporated herein by reference in its entirety. The embodiment shown in FIG. 6 includes a cross-shaped locking mechanism that may, for example, be inserted into the locking member of the exemplary delivery device in FIG. 5 and twisted to "lock" the implantable device to the core cannula for delivery to a particular portion of a patient (e.g., the patient's left atrial appendage).

FIGS. 7-10 show various cross sections of an access sheath, catheter, and/or delivery device attached to an exemplary implantable device as described herein. In the embodiments shown, the delivery device includes a core cannula, an injection apparatus extending through the core cannula and into an implantable device, and a device locking member operatively connected to the implantable device.

Figure 7:
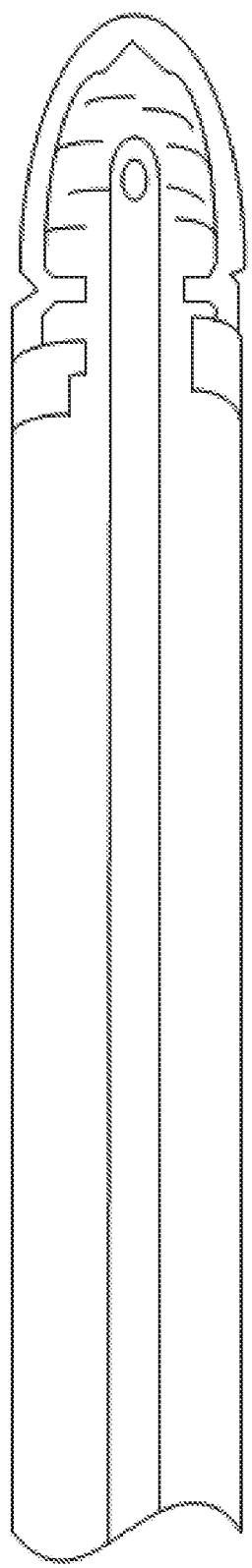
FIG. 7 shows a cross section of an exemplary delivery device attached to an exemplary occlusion device, according to one embodiment of the present disclosure.
Figure 8:
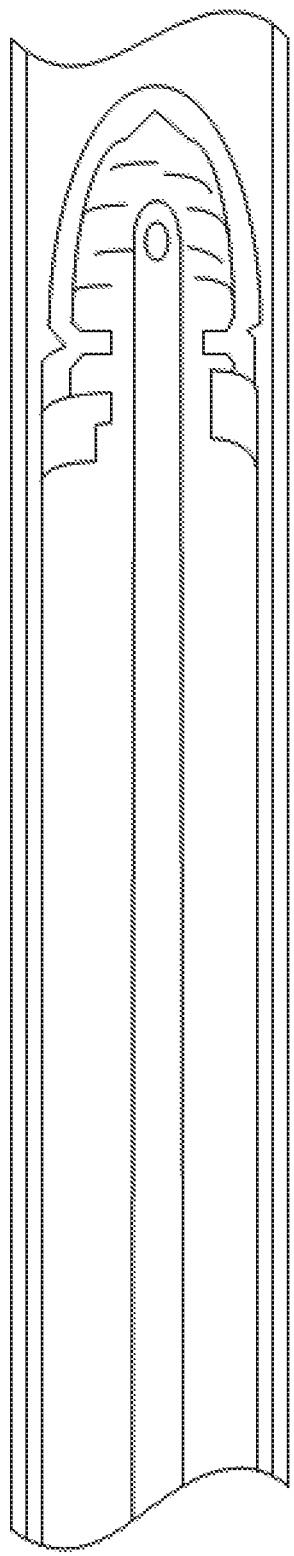
FIG. 8 shows a cross section of an exemplary delivery device attached to an exemplary occlusion device within an exemplary access sheath, according to one embodiment of the present disclosure.
Figure 9:
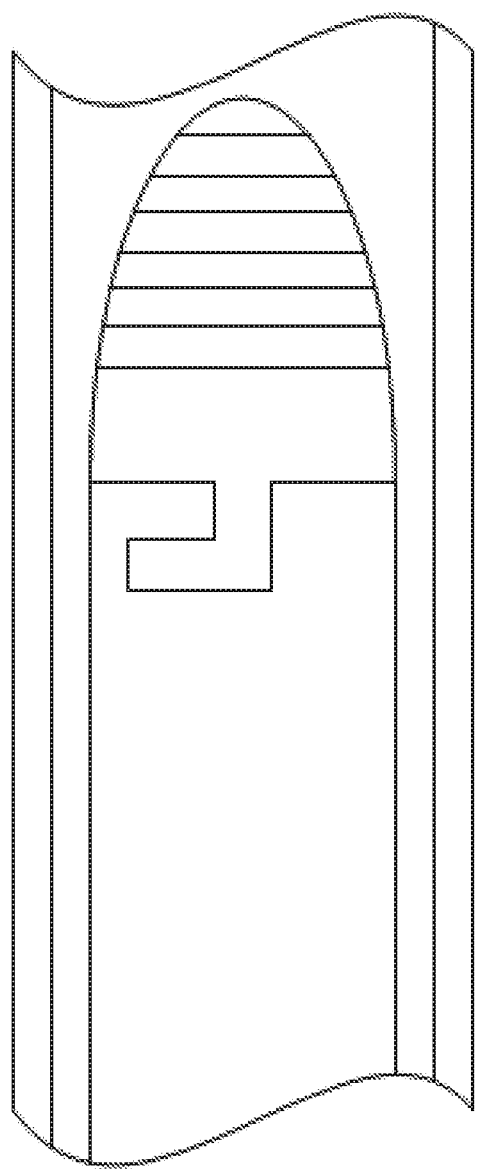
FIG. 9 shows a cross section of an exemplary access sheath with an exemplary delivery device attached to an exemplary occlusion device within, according to one embodiment of the present disclosure.
Figure 10:
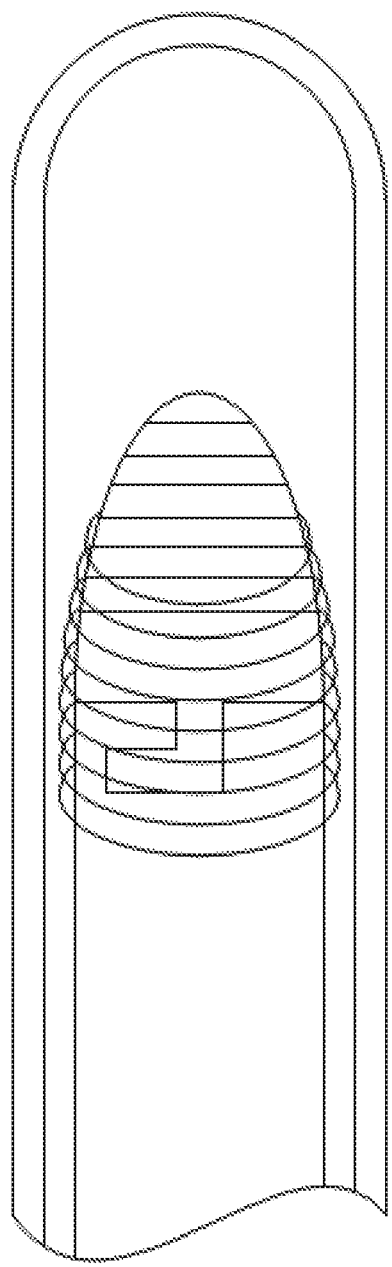
FIG. 10 shows a cross section of an exemplary access sheath with an exemplary delivery device with expanding members attached to an exemplary occlusion device within, according to one embodiment of the present disclosure.

FIG. 7 shows a cross section of the exemplary delivery device attached to the exemplary implantable device. FIG. 8 shows a cross section of the access sheath and/or catheter and the delivery device and implantable device within. FIG. 9 shows a cross section of the access sheath and/or catheter and the exterior of the core cannula and implantable device (attached via the exemplary locking member). FIG. 10 shows a cross section of an exemplary access sheath/catheter and an exterior of the core cannula and implantable device, with expandable members attached. In the embodiment shown, the expandable members are compressed in a first position within a catheter and/or access sheath prior to being inserted into a body, where they may be expanded upon exiting the catheter and/or access sheath.

The exemplary delivery system shown in FIGS. 7-10 will be navigated from a user end access point through the access sheath/catheter to a destination to deploy an exemplary implantable device. The distance tolerance between an exemplary delivery system and access sheath will be such (e.g., 0.3333 mm, 0.6666 mm, 1 mm, etc.) to allow smooth navigation of an exemplary delivery system. An exemplary delivery system can be navigated within an access sheath/catheter through bodily fluids such as blood or other fluids such as saline, sterile water, etc. or a combination of the aforementioned fluids.

Exemplary Device Use Case

Figure 11:
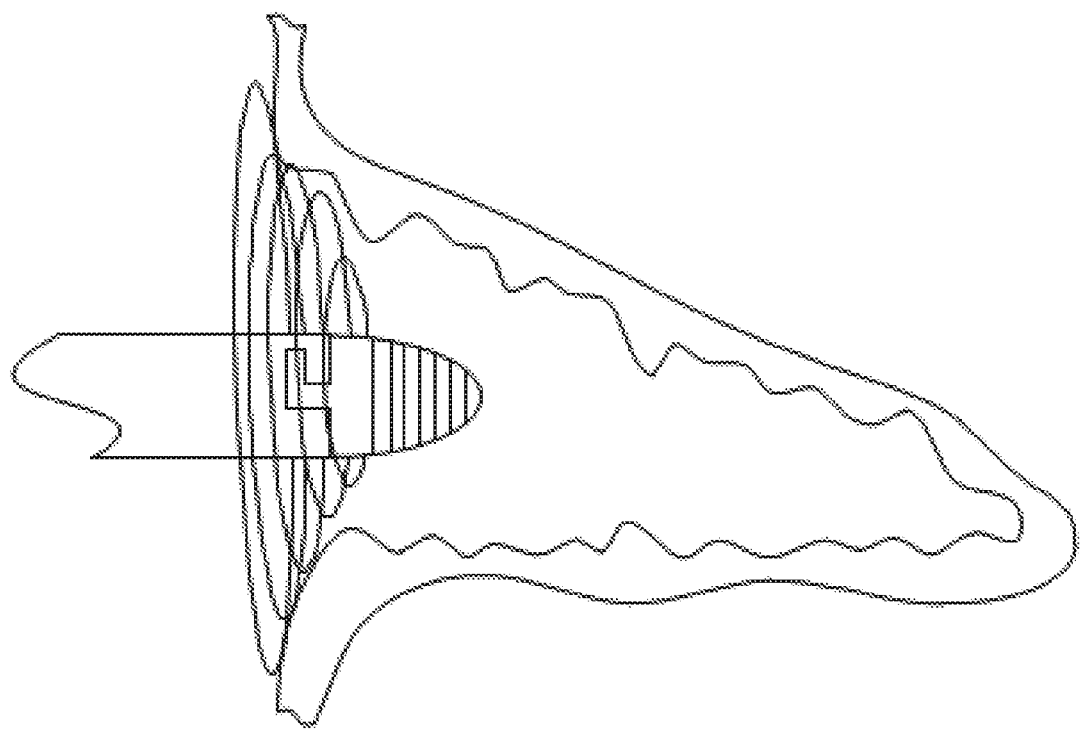
FIG. 11 shows a cross section of an exemplary LAA with an exemplary delivery device attached to an exemplary occlusion device, according to one embodiment of the present disclosure.
Figure 12:
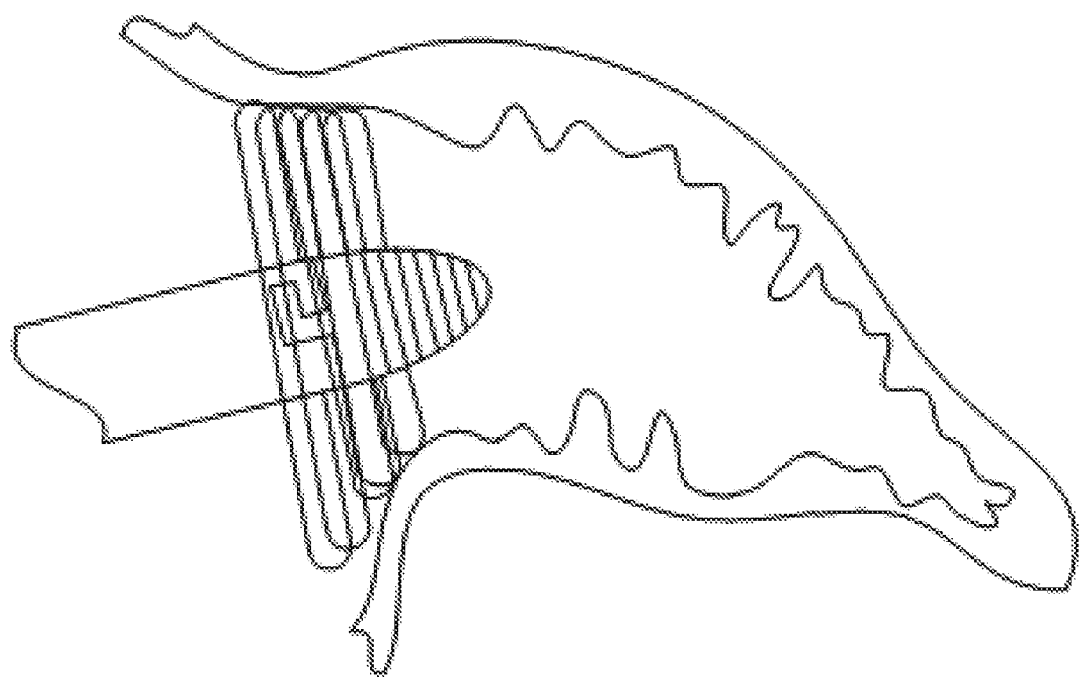
FIG. 12 shows a cross section of an exemplary LAA with an exemplary delivery device attached to an exemplary occlusion device, according to one embodiment of the present disclosure.
Figure 13:
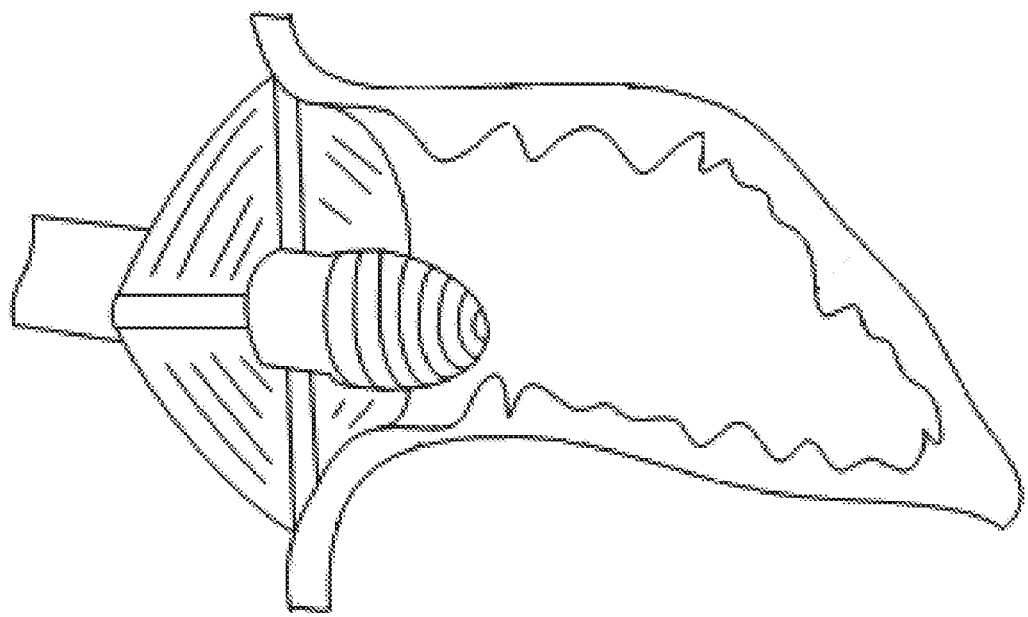
FIG. 13 shows a cross section of an exemplary LAA with an exemplary delivery device attached to an exemplary occlusion device, according to one embodiment of the present disclosure.

FIGS. 11-13 depict an exemplary delivery system use case. In particular, FIGS. 11-13 depict an exemplary delivery system used for inserting an attached implantable device into a left atrial appendage (LAA) within a patient's heart. Exemplary delivery systems described herein may be used to deliver an implantable device to occlude the LAA to, for example, help prevent a stroke in the patient. Due to a high prevalence of thrombus formation in the LAA of atrial fibrillation (AF) patients, occluding the LAA may prevent a majority of thrombus formation and thus reduces the risk of ischemic stroke.

Delivering a left atrial appendage closure (LAAC) for a particular patient is briefly described, as shown in FIGS. 11-13. Delivery device component numbers used in FIGS. 1-4 will be used throughout this description. This exemplary procedure is included to further promote an understanding of the exemplary devices and processes disclosed herein and is not necessarily intended to be limiting. The exemplary LAAC procedure for the particular patient may be done under local or general anesthesia in a catheterization lab using standard transseptal techniques. The exemplary procedure may last about one hour and the patient will stay overnight at a hospital post implantation in order to monitor any adverse effects.

In particular embodiments, imaging techniques, such as transesophageal echocardiography (TEE), will be performed to measure the LAA to determine device size. The procedure is then performed under appropriate imaging, which may include fluoroscopic, intracardiac echocardiographic (ICE), or TEE guidance. A transseptal needle attached to a guidewire (not shown) will then puncture the intraatrial septum, allowing for the transseptal access sheath 40 to advance over the transseptal needle and through the puncture within the intraatrial septum into the left atrium. The transseptal needle and the guidewire are then removed from the system. An adhesive or locking mechanism (not shown) will be attached to the transseptal access sheath 40 to prevent movement of the sheath 40. The transseptal access sheath 40 contains a hemostasis valve 48 to prevent backflow of bodily fluid. A delivery catheter embodiment 42 is then advanced through the access sheath 40 to aid in directing the implantable device. A core cannula 32 with a proximal or user and distal or device end can then be advanced through the access sheath 40, where the distal end of the core cannula 32 includes a portion to aid in eventual placement of the implantable device. The core cannula 32 is directed through the body to the targeted body cavity, for example, the left atrial appendage, under fluoroscopic, ICE, or TEE guidance. Once the distal portion of the core cannula 32 exits the access sheath 40, expandable members 38 attached to the distal portion of the core cannula 32 will move from a first position (within the access sheath) to a second, expanded position to allow the implant device to expand in a position inside a body cavity, while keeping the device flush or in the same plane with nearby tissue.

As discussed herein, the expandable members 38 can be constructed as a wire from a self-expanding, super elastic element, such as Nitinol, etc. and can be coated or enclosed by chemical or physical means, such as a polymeric, elastomeric material, etc. to prevent harm towards neighboring bodily structures. In one embodiment, once the expandable members 38 have exited the access sheath 40, the expandable members 38 will expand to a pre-determined shape, such as a round, ovular, cross, diamond, spring etc. formation. The expandable members 38 along with the core cannula 32 are advanced towards the opening of the body cavity until the expandable members 38 reach the opening and engage with the surrounding tissue, preventing the core cannula 32 from advancing further. The expanding members 38 may be constructed to take into account varying sizes of the body cavity and can be sized incrementally (e.g., gradient of 1 mm, 1.5 mm, 2 mm, etc.) in the form of a spring basket (e.g., as shown in FIGS. 11 and 12). The proximal end of the expandable members 38 can be relatively larger compared the to the distal portion in order to account for larger LAA orifice diameters. The most distal portion of the expandable members 38 may be incrementally (e.g., gradient of 1 mm, 1.5 mm, 2 mm, etc.) tapered or veer slightly inwards to account for smaller LAA orifice diameters and to avoid penetrating surround bodily structures. The position of the core cannula 32 can then be locked at the proximal end that may include an adhesive, twisting method, or another locking mechanism (not shown). As will be understood by one of ordinary skill in the art, compressed and expanded diameters of the expandable members may vary based on application. Such as, for example, should a patient have a smaller LAA or the surrounding bodily cavity be smaller than average, expandable members that have a smaller than average expanded diameter may be used to prevent damage to surrounding tissue.

According to particular embodiments, once the expandable members 38, core cannula 32, and implantable device are in place, an injection apparatus 34 with a proximal and distal end is inserted through the core cannula 32 and travels to the body cavity (as will be understood by one of ordinary skill in the art, an injection apparatus 34, in various embodiments, may be pre-inserted in the core cannula 32 and the implantable device). In various embodiments, the proximal end of an injection apparatus 34 includes an injection apparatus handle 46 to manipulate the length and position of an injection apparatus 34 as well as to reduce the risk of advancing an injection apparatus 34 through the entirety of the body cavity during the pre-insertion period. In particular embodiments, the distal end of the core cannula 32 is pre-attached to the implantable device through the device locking member 36, which may include a twisting system, luer lock system, etc. In one or more embodiments, the distal end of an injection apparatus 34 is pre-inserted or moved inside the implantable device to allow for fluid ejection. In particular embodiments, a fluid is injected into an injection apparatus 34 through a syringe (not shown) until the device has successfully occluded the body cavity (as discussed in applications incorporated by reference herein). In at least one embodiment, upon assessment of successful occlusion through imaging and final contrast injections, an injection apparatus 34 is removed, and the core cannula is detached from the implantable device via the device locking member 36 via a twisting method, at the device deployment handle 44 found on the proximal end of the core cannula 32. In one embodiment, the device deployment handle 44 further includes one or more injection apparatus handles 46 that are operatively connected to an injection apparatus 34. In particular embodiments, the distal end of the core cannula 32 detaches from the implantable device and is removed from the patient along with the access sheath 40. Following the retrieval of the core cannula 32, attached expandable members 38 are compressed into the access sheath 40.

Alternate Embodiments

In a first alternate embodiment, an exemplary device may include expandable members of varying locations on the delivery system. In this first alternate embodiment, a shape memory structure (such as nitinol or PEEK) can be attached at a proximal end, a distal end, or other locations along the length of the exemplary delivery device. Continuing with this embodiment, the length of the shape memory structure may range from a portion to the entire length of the delivery system. In this alternate embodiment, the shape memory material may be fabricated through braiding, laser cutting, or wiring to allow for differentiating morphologies. As will be understood by one of ordinary skill in the art, heat treatments may also be applied to the shape memory material to yield independent shapes.

Various embodiments of the device herein are depicted as multiple cannulae with eggbeater-shaped expandable members, but the expandable members may be in suitable alternate shapes, including cylindrical, ovular, cross-shaped, multiangular, or coil-shaped. Further, in particular embodiments, the expandable members may be attached to each other with adhesives or shape memory material. In some embodiments, the expansion of the expanding members could be mechanically manipulated through attached wiring, threading, or a balloon that can expand via user control.

Figure 14:
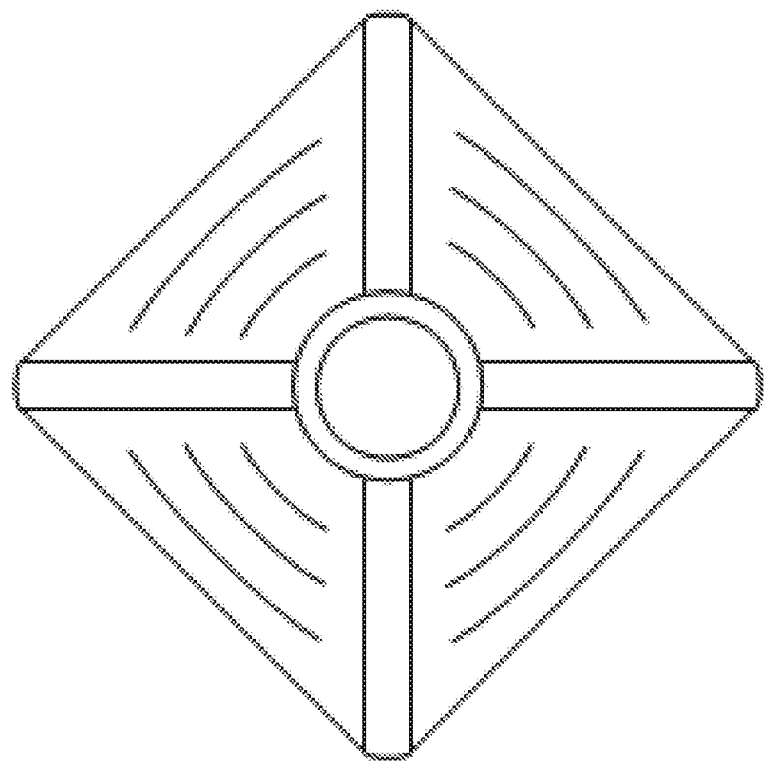
FIG. 14 shows a front view of an alternate embodiment of expanding members for use with an exemplary delivery system, according to one embodiment of the present disclosure.

As shown in FIG. 14, in some embodiments, an exemplary device may include features to further prevent thrombus migration from the LAA. In such embodiments (and others), the expandable members may be attached to an occluding fabric made of PTFE, PET, or various woven fabrics.

In particular embodiments, the delivery system may have multiple steering stages, wherein each stage can move in multiple planes. The steering stages may integrate multiple shape memory wires that are heat treated to independently control the wire configurations and the consequent steering stages. The steering capability can be controlled by methods (e.g., trigger, switch, etc.) found on the user end of an exemplary delivery system. This delivery system with multiple steering stages could be implemented for various scenarios, including delivering implantable technologies, angioplasty, valve repair, and drug therapy. In alternate embodiments, the point of attachment between the delivery system and device can vary. Attachment systems include luer-lock systems, anti-rotation systems, microscrew mechanisms. In other embodiments, the location of the attached device to the delivery system may vary, including being within the expanding members or located proximally or distally in relation to the expanding members. In further alternate embodiments, the delivery system may not be detachable from a connected device. In scenarios, such as angioplasty, a balloon or attached device may be attached to the delivery system through adhesives, molding, or welding.

In various embodiments, the distal end of the delivery system may contain a sensor unit. In such embodiments, the sensor unit's purpose may include but not limited to detection of thrombus, physiological function, sterility, or microbial activity.

In some embodiments, a coating may be applied to the delivery system. The purpose of the coating may include but not limited to lubricity, microbial stability, fluid absorption, and encrustation reduction. In alternate embodiments, the material of the delivery system may be induced with elements, such as tungsten or silver, to increase levels of radiopacity, microbial stability, allergy reduction, durability, or sterility.

In particular embodiments, the various tube-like components (e.g., core cannula, access sheath, etc.) of the delivery system may be mechanically or chemically enhanced to increase flexibility or durability. In a particular embodiment, a coil could be integrated within the core cannula through molding or welding techniques for increased functionality. Continuing with this embodiment, the tightness or pitch of the wound coil along the length of the core cannula may vary. In an alternative embodiment, the coil could also be braided.

In some embodiments, more than one injection apparatus may be inserted into the delivery system. This may be applicable in scenarios requiring delivery of multiple injectable fluids or fluids that require at least a two-part mixture. Examples of such injectable materials include hydrogels, occlusion gels, etc.

In various embodiments, the device attached to the delivery system may be a balloon. In alternate embodiments, a device with expandable members (e.g. nitinol) may be delivered through the delivery system. Alternatively, in particular embodiments, a device with woven fiber (e.g. PET, ePTFE, Dacron) may be deployed through the delivery system.

The delivery system may be used for identification of general soft tissue concavities or areas in need of occlusion. In various embodiments, the expandable elements of the delivery system allow for precise deployment of an attached device. In some embodiments, these characteristics may be appropriate for closure of atrial septal defects (ASDs) and patent foramen ovales (PFOs), which are defects found in the atrial septal wall. Alternatively, the core cannula elements along with the functionality of the delivery system could be used for drug delivery to a blood vessel during angioplasty. In particular embodiments, the delivery system may be intended for balloon valvuloplasty to mechanically force the opening of a narrowed heart valve. In further embodiments, a drug eluting element may be added to reduce further calcification.

CONCLUSION

Accordingly, the reader will see that the aforementioned delivery system can be used to easily deploy an implantable, expandable device into a body cavity, such as a LAA, easy-to-use system to deploy the device, and allows the device to be flush against the surrounding tissue.

While the above description contains many specificities, these should not be construed as limitations on the scope of any embodiment, but as exemplifications of various embodiments thereof. Many other ramifications and variations are possible within the teachings of the various embodiments. For example, the attachment embodiments may differ compared to the drawings, the delivery system may alter in shape, size, and multiple similar devices could be used for other applications, etc.

Thus the scope should be determined by the appended claims and their legal equivalents, and not by the examples given.

We claim:

1. An apparatus for delivering a medical device to one or more bodily orifices, the apparatus comprising:
   a substantially cylindrical core cannula having a proximal end and a distal end;
   a hollow access sheath, wherein the core cannula, a locking member, and a plurality of expandable members are threaded through the hollow access sheath upon deployment;
   the locking member operatively coupled to the distal end of the core cannula;
   the plurality of expandable members coupled to the distal end of the core cannula, wherein the plurality of expandable members:
     are configured for expanding from a compressed position to an expanded position;
     are in the compressed position within the hollow access sheath and self-expand to the expanded position upon exiting the hollow access sheath; and
     comprise a second proximal end and a distal portion opposite the second proximal end, wherein a subset of the plurality of expandable members located toward the second proximal end are sized larger than a second subset of the plurality of expandable members located toward the distal portion;
   one or more injection apparatuses inserted into a hollow portion along a length of the core cannula, the one or more injection apparatuses defining at least one opening at a distal end for transmitting fluid; and
   a device deployment handle operatively connected to the proximal end of the core cannula for detaching a device operatively connected to the locking member by twisting the device deployment handle.

2. The apparatus of claim 1, wherein the apparatus further comprises at least one injection apparatus handle, the at least one injection apparatus handle coupled to the one or more injection apparatuses for manipulating a position of the one or more injection apparatuses.

3. The apparatus of claim 2, wherein the at least one injection apparatus handle further includes one or more access ports for injecting fluid into the one or more injection apparatuses.

4. The apparatus of claim 1, wherein the apparatus further comprises a hemostasis valve at a proximal end of the hollow access sheath for preventing backflow of bodily fluid.

5. The apparatus of claim 1, wherein each of the plurality of expandable members comprises a substantially circular cross section expandable from a first diameter in the compressed position to a second diameter in the expanded position.

6. The apparatus of claim 5, wherein the second diameter of at least one of the plurality of expandable members is defined by a bodily cavity.

7. The delivery system of claim 1, wherein the device deployment handle is adhered to the proximal end of the core cannula.

8. The delivery system of claim 1, wherein the plurality of expandable members comprises a plurality of self-expanding wire-like members.

9. The delivery system of claim 8, wherein the plurality of self-expanding wire-like members are incrementally sized.

10. The delivery system of claim 1, wherein the length of the core cannula measures at least 75 cm between the proximal end of the core cannula and the distal end of the core cannula.

11. A medical device delivery system, the delivery system comprising:
    a substantially cylindrical core cannula having a proximal end and a distal end;
    a hollow access sheath surrounding a portion of the length of the core cannula, a locking member, and a plurality of expandable members;
    the locking member operatively coupled to the distal end of the core cannula;
    the plurality of expandable members coupled to the distal end of the core cannula, wherein the plurality of expandable members:
      have a substantially circular cross-section;
      are compressible from an expanded position to a compressed position; and
      are in the compressed position within the hollow access sheath and self-expand to the expanded position upon exiting the hollow access sheath; and
      comprise a proximal end and a distal portion opposite the proximal end, wherein a subset of the plurality of expandable members located toward the proximal end are sized larger than a second subset of the plurality of expandable members located toward the distal portion;
    a substantially cylindrical injection apparatus inserted into a hollow portion along a length of the core cannula, the injection apparatus defining at least one opening at a distal end for transmitting fluid; and
    a device deployment handle operatively connected to the proximal end of the core cannula for detaching a device operatively connected to the locking member by twisting the device deployment handle.

12. The delivery system of claim 11, wherein the delivery system further comprises an injection apparatus handle, the injection apparatus handle coupled to the injection apparatus for manipulating a position of the injection apparatus.

13. The delivery system of claim 12, wherein the injection apparatus handle further includes one or more access ports for injecting fluid into the injection apparatus.

14. The delivery system of claim 11, wherein the delivery system further comprises a hemostasis valve at a proximal end of the hollow access sheath for preventing backflow of bodily fluid.

15. The delivery system of claim 11, wherein the substantially circular cross section of each of the plurality of expandable members is expandable from a first diameter in the compressed position to a second diameter in the expanded position, wherein the second diameter of at least one of the plurality of expandable members is defined by a bodily cavity.

16. The delivery system of claim 11, wherein the locking member includes one or more substantially L-shaped channels for interfacing with one or more extrusions from the device.

17. The delivery system of claim 11, wherein the device deployment handle is adhered to the proximal end of the core cannula.

18. The delivery system of claim 11, wherein the plurality of expandable members comprises a plurality of self-expanding wire-like members.

19. The delivery system of claim 18, wherein the plurality of self-expanding wire-like members are incrementally sized.

20. The delivery system of claim 11, wherein the length of the core cannula measures at least 75 cm between the proximal end of the core cannula and the distal end of the core cannula.

* * * * *